United States Patent
Deshpande et al.

(10) Patent No.: US 11,147,779 B2
(45) Date of Patent: Oct. 19, 2021

(54) THERAPEUTIC AGENT FOR PHOSPHODIESTERASE INHIBITION AND ITS RELATED DISORDERS

(71) Applicants: Novalead Pharma INC, Allendale, NJ (US); Supreet K. Deshpande, Pune (IN)

(72) Inventors: Supreet K. Deshpande, Pune (IN); Sudhir A. Kulkarni, Pune (IN); Atul S. Aslekar, Pune (IN)

(73) Assignees: Supreet K. Deshpande, Allendale, NJ (US); Novalead Pharma Inc, Allendale, NJ (US)

( * ) Notice: Subject to any disclaimer, the term of this patent is extended or adjusted under 35 U.S.C. 154(b) by 0 days.

(21) Appl. No.: 16/495,939

(22) PCT Filed: Mar. 14, 2018

(86) PCT No.: PCT/IN2018/050140
§ 371 (c)(1),
(2) Date: Sep. 20, 2019

(87) PCT Pub. No.: WO2018/173069
PCT Pub. Date: Sep. 27, 2018

(65) Prior Publication Data
US 2020/0022931 A1 Jan. 23, 2020

(30) Foreign Application Priority Data
Mar. 21, 2017 (IN) .............................. 201721009758

(51) Int. Cl.
*A61K 31/167* (2006.01)
*A61P 17/06* (2006.01)
*A61K 9/00* (2006.01)
*A61K 9/06* (2006.01)
*A61K 31/426* (2006.01)
*A61K 47/06* (2006.01)
*A61K 47/44* (2017.01)

(52) U.S. Cl.
CPC .......... *A61K 31/167* (2013.01); *A61K 9/0014* (2013.01); *A61K 9/0019* (2013.01); *A61K 9/0048* (2013.01); *A61K 9/0053* (2013.01); *A61K 9/0075* (2013.01); *A61K 9/0078* (2013.01); *A61K 9/06* (2013.01); *A61K 31/426* (2013.01); *A61K 47/06* (2013.01); *A61K 47/44* (2013.01); *A61P 17/06* (2018.01)

(58) Field of Classification Search
None
See application file for complete search history.

(56) References Cited

U.S. PATENT DOCUMENTS

2006/0035979 A1  2/2006  Callahan et al.
2017/0056347 A1* 3/2017  Glick ...................... A61P 29/00

FOREIGN PATENT DOCUMENTS

GB   2450608 A  * 12/2008 .............. A61P 17/02
WO   WO-2004006906 A2 * 1/2004 ......... A61K 31/4745

* cited by examiner

Primary Examiner — Samantha L Shterengarts
(74) Attorney, Agent, or Firm — Forge IP, PLLC

(57) ABSTRACT

The pharmaceutical composition for treatment of phosphodiesterase related disorders comprises of administering to the subject a therapeutically effective amount of a compound of Formula-I, or compounds selected from the group consisting of Niclosamide, Oxyclozanide, Rafoxanide, Closantel, Dibromsalan, Metabromsalan. Tribromsalan and Nitazoxanide, and prodrugs, metabolites, or pharmaceutically acceptable salts, solvates and polymorphs thereof in a pharmaceutically acceptable carrier, vehicle, or diluents.

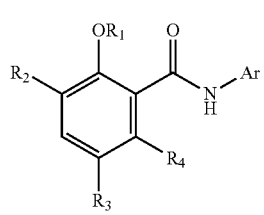

8 Claims, No Drawings

THERAPEUTIC AGENT FOR PHOSPHODIESTERASE INHIBITION AND ITS RELATED DISORDERS

FIELD OF THE INVENTION

The present disclosure relates to treatment of phosphodiesterase (PDE) related disorders.

BACKGROUND OF THE INVENTION

A phosphodiesterase is an enzyme class that breaks a phosphodiester bond. The cyclic nucleotide phosphodiesterases (PDE) comprise a group of enzymes that degrade the phosphodiester bond in the second messenger molecules namely cAMP (cyclic adenosine monophosphate) and cGMP (cyclic guanosine monophosphate). They regulate the localization, duration, and amplitude of cyclic nucleotide signaling within subcellular domains. PDEs are therefore important regulators of signal transduction mediated by these second messenger molecules. PDEs are also downstream effectors of cAMP and cGMP. PDEs are closely related to the regulation of each specific transduction signal, and therefore multiple PDEs play important roles in modulating each cellular function.

The PDE superfamily of enzymes is classified into 11 families, namely PDE1 to PDE11, in mammals. Different PDEs of the same family are functionally related despite the fact that their amino acid sequences can show considerable divergence. PDEs have different substrate specificities. Some are cAMP selective hydrolases (PDE4, PDE7 and PDE8), while others are cGMP selective (PDE5, PDE6 and PDE9). Others can hydrolyze both cAMP and cGMP (PDE1, PDE2, PDE3, PDE10 and PDE11). There is evidence that many of these PDEs are tightly connected to different physiological functions in the body and hence by inference also to different pathological conditions. Another significant factor in the regulation of PDEs and their role in the cyclic nucleotide metabolism is the fact that PDE isoenzymes and families tend to be very tissue-specific.

PDE enzymes are often targets for pharmacological inhibition due to their unique tissue distribution, structural properties, and functional properties. Inhibitors of PDE can prolong or enhance the effects of physiological processes mediated by cAMP or cGMP by inhibition of their degradation by PDE. Selective and non-selective PDE inhibitors have been identified as new potential therapeutics for several diseases. Selective PDE inhibitors are being used as well as investigated in a wide range of diseases including:

(i) PDE1 inhibitor Vinpocetine has been investigated in clinical trials for its neuroprotective effects. Vinpocetine also has antioxidant effects and antiulcer activity.

(ii) PDE2 inhibitors have been explored for their use in sepsis, cognitive disorders and Acute Respiratory Distress Syndrome (ARDS).

(iii) PDE3 inhibitors are used for intermittent claudication and proposed for use in Airways disease and fertility (male and female contraceptives). PDE3 inhibitor also has shown anti-asthmatic effects by both anti-inflammatory and bronchodilator properties. In the treatment of atopic dermatitis, the mixed PDE3-PDE4 inhibitor Zardaverine was a more potent inhibitor of T cell proliferation than Rolipram, a selective PDE4 inhibitor.

(iv) PDE4 inhibitors have shown potential to treat asthma, COPD, allergic rhinitis, psoriasis, multiple sclerosis, depression, Alzheimer's disease, memory loss, cancer, dermatitis and schizophrenia. Pentoxifylline, a PDE4 inhibitor, has the potential to enhance circulation and may have applicability in treatment of diabetes, fibrotic disorders, peripheral nerve damage, and microvascular injuries. PDE4 inhibitors have also shown potential in the treatment of AIDS, arthritis like rheumatoid-, psoriatic- and osteo-arthritis, bronchitis, endotoxin shock, inflammatory bowel diseases like ulcerative colitis and Crohn's disease, adult respiratory distress syndrome (ARDS), allergic conjunctivitis, dry eye disorder and other inflammatory diseases. PDE4 inhibitors suppress the release of cytokines and other inflammatory signals, and inhibit the production of reactive oxygen species. Crisaborole is a nonsteroidal, topically administered, boron-containing, anti-inflammatory compound that inhibits PDE4 activity and thereby suppresses the release of TNF-α, IL-12, IL-23 and other cytokines. Crisaborole is approved for the treatment of mild-to-moderate atopic dermatitis (eczema) in patients 2 years of age and older. Phase I and phase II trials of Crisaborole in patients with psoriasis have also been completed. Apremilast which is also a PDE4 inhibitor has been approved for treatment of psoriatic arthritis and psoriasis. PDE4 inhibitors have been demonstrated to be beneficial in the treatment of lung inflammation and fibrosis.

(v) PDE5 inhibitors have been used to treat erectile dysfunction, sexual dysfunction in females, cardiovascular disease, premature ejaculation, stroke, leukemia and renal failure. Sildenafil (PDE5 inhibitor) is also currently being investigated for its myo- and cardioprotective effects, with particular interest being given to the compound's therapeutic value in the treatment of Duchenne muscular dystrophy. PDE5 is abundantly expressed in lung tissue, and appears to be upregulated in pulmonary arterial hypertension (PAH). PDE5 inhibitors Sildenafil and Tadalafil are two of the recommended first-line therapies for PAH patients in World Health Organization functional classes II or III.

(vi) PDE7 inhibitors have been used in inflammatory diseases. PDE7A inhibitor compound ASB16165 has been shown to inhibit T lymphocyte activation and suppresses skin inflammation and impair proliferation of keratinocytes both in vitro and in vivo. Studies indicate PDE7A might regulate TNF-α production in keratinocytes in a cAMP-dependent fashion and have reduced skin inflammation in animal model. Specific inhibitors of PDE7 have also been reported as potential new drugs for the treatment of neurological disorders because of their ability to increase intracellular levels of cAMP.

(vii) PDE9 inhibitors have been explored for treatment of Alzheimer's disease.

(viii) PDE10 inhibitors have shown potential in treatment of Schizophrenia and Huntington's disease.

Non-selective PDE inhibitors such as Caffeine, Aminophylline, Pentoxyphylline, Theophylline etc. have the potential to enhance circulation and may have applicability in treatment of diabetes, fibrotic disorders, peripheral nerve damage, and microvascular injuries or as bronchodilators. Thus, even nonselective phosphodiesterase inhibitors have therapeutic utility and have been shown to inhibit TNF-α and leukotriene synthesis and reduce inflammation and innate immunity.

Inflammatory cells such as Basophils, B-lymphocytes, Dendritic cells, Endothelial cells, Eosinophils, Macrophages, Mast cells, Monocytes, Neutrophils and T-lymphocytes express various PDEs at different levels and inhibition of PDEs in these cells can lead to anti-inflammatory effects in different tissues. These cells are also involved in several immunological functions and are involved in pathogenesis of many diseases.

Phosphodiesterase inhibitors have shown efficacy in treatment of a variety of inflammatory skin diseases. Skin diseases such as psoriasis, dermatitis or eczema, acne, rosacea have complex pathology, with some common pathways involving in many of these diseases. Some of the skin diseases such as acne and dermatitis may be triggered from bacterial infections but may also have an inflammatory component. Alternatively, inflammatory skin diseases are triggered by causes other than bacterial infection (non-infectious origin), e.g. immune system disorder, medication, food allergy, emotional stress, UV radiation, soaps and fragrances, allergens, etc. In a group of embodiments, the compounds of Formula I described herein are suitable for treatment of inflammatory skin conditions such as psoriasis, rosacea or dermatitis. In another group of embodiments, the compounds of Formula I described herein are suitable for treatment of inflammatory skin conditions such as psoriasis or rosacea. In an alternate group of embodiments, the compounds of Formula I described herein are suitable for treatment of secondary inflammation associated with skin conditions which may be initially triggered by bacterial infections. In further embodiments, the compounds of Formula I described herein are suitable for treatment of dermatitis or eczema not associated with or originating from an underlying microbial infection.

Psoriasis includes, and is not limited to, plaque psoriasis (psoriasis vulgaris), guttate psoriasis, inverse psoriasis, erythrodermic psoriasis and pustular psoriasis having varied clinical signs and incidences amongst psoriatic population. Dermatitis includes, and is not limited to, atopic dermatitis, contact dermatitis, stasis dermatitis, dyshidrotic dermatitis, nummular dermatitis, neurodermatitis, seborrheic dermatitis and the like. Rosacea includes, and is not limited to, erythematotelangiectatic rosacea, papulopustular rosacea, phymatous rosacea, ocular rosacea and the like. Effective treatment of skin diseases like psoriasis, rosacea and dermatitis requires management of different inflammatory processes involved in the pathogenesis of the disease.

Psoriasis is characterized by hyperplasia of epidermal keratinocytes, angiogenesis, and infiltration of T-lymphocytes, neutrophils, and other types of leukocyte in the affected skin. The proliferative keratinocyte response is thought to be due to activation of the cellular immune system, with T-cells, dendritic cells, and various immune-related cytokines and chemokines implicated in pathogenesis. Further, histamine and proteases play a role in the pathogenesis of psoriasis. Currently, psoriasis has been considered as a T-lymphocyte-mediated autoimmune disease, and new biological therapies that target T-cells have just entered routine clinical practice as IL-17 and IL-23 monoclonal antibodies indicating importance of IL-17/IL-23 axis in pathogenesis of psoriasis. However, current observations suggest that although activated T-lymphocytes have an undisputed role in the pathogenesis of psoriasis, there are other regulatory systems that contribute to the inflammatory and proliferative processes of psoriasis. The current pathogenesis of psoriasis involves keratinocytes, NK T cells, plasmacytoid dendritic cells, macrophages which release several cytokines like TNF-α, IL-6, IL-1, IFN-γ leading to activation of myeloid dendritic cells which release IL-23 and IL-12 to activate Th-17 and Th-1 cells. The activated Th-17 cells release cytokines like IL-17A, IL-17F and IL-22, whereas activated Th-1 cells release TNF-α and IFN-γ which activate keratinocytes which in turn release several cytokines and chemokines thereby continuing the diseases state. PDE inhibition has shown to have reduced cytokines involving IL-17/IL-23 axis. One such regulatory system involves cyclic nucleotides that play key role in psoriasis. The mediator system, cAMP– cGMP as an off-on system, is not as simple as once perceived and cAMP can either stimulate or inhibit cell proliferation. The PDE inhibitors Aminophylline and Theophylline, which increase cAMP levels, have been shown to be of benefit in the treatment of psoriasis.

Increased cAMP-phosphodiesterase activity in peripheral blood leukocytes is associated with the immune and inflammatory hyper reactivity that characterizes atopic dermatitis. Atopic dermatitis is responsive to a variety of enzyme inhibitors. The ability of selective high-potency PDE inhibitors to reduce prostaglandin E2, IL-10, and IL-4 production in atopic mononuclear leukocyte cultures has been demonstrated in vitro. A clinical study of a PDE4 inhibitor in 20 patients with atopic dermatitis demonstrated significant reductions of all inflammatory parameters. PDE inhibitors modulate several pathways contributing to the exaggerated immune and inflammatory responses, which characterize atopic dermatitis. Thus, PDE inhibitors may provide a useful alternative to the over-reliance on corticosteroid therapy in atopic diseases like psoriasis, eczema and rosacea. Further, involvement of IL-23 and Th17 cytokines has been described in allergic contact dermatitis which shows involvement of cytokines like IL-17A, IL-17F and IL-22 in the disease.

Rosacea is a chronic and potentially life-disruptive disorder primarily of the facial skin inflammation, often characterized by flare-ups and remissions. It is observed as a redness on the cheeks, nose, chin or forehead. In some cases, rosacea may also occur on the neck, chest, scalp or ears; which is may be due to factors related to blood flow, skin bacteria, microscopic skin mites (Demodex), irritation of follicles, sun damage of the connective tissue under the skin, an abnormal immune or inflammatory response, or psychological factors. Apremilast (PDE4 inhibitor) has been investigated for the treatment of rosacea on a small population and has shown promising results. Recent study shows involvement of Th1/Th17 cells in pathogenesis of all sub-types of rosacea.

PDE inhibitors can provide alternatives for treatment of fibrotic skin diseases through various routes of administration, including topical administration. Sildenafil, a PDE5 inhibitor is an effective drug to treat the manifestations of scleroderma vasculopathy, such as Raynaud's phenomenon (RP), digital ulcers (DU) and/or necroses (N), and pulmonary hypertension (PH). Thus, both cyclic nucleotides (cAMP and cGMP) specific PDE inhibitors can provide treatment options in scleroderma. This is exemplified by use of the PDE3 inhibitor Cilostazol for treatment of Raynaud's syndrome (RS).

Thus, PDE inhibitors can play key role in alleviation of several immune and &in diseases. Many of these immune and skin diseases are treated with corticosteroids and drugs having several limitations and safety issues. Therefore, there is a need for safe and effective compositions for treatment of PDE related disorders.

SUMMARY OF THE INVENTION

This disclosure is based in part on the finding that certain anti-parasitic drugs (e.g., certain anti-helminthic drugs, certain anti-protozoal drugs) inhibit phosphodiesterases. Disclosed herein is the finding that compositions comprising compounds of Formula-I are useful for treating phosphodiesterase related disorders in a mammal,

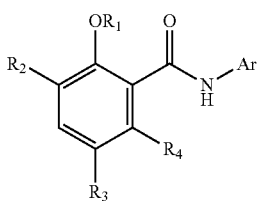

wherein R1 is —H or —COCH₃; R₂ is —H, —Cl, —Br, or —I; R₃ is —H, —Cl, —Br, or —I; R₄ is —H. or —Cl; Ar is

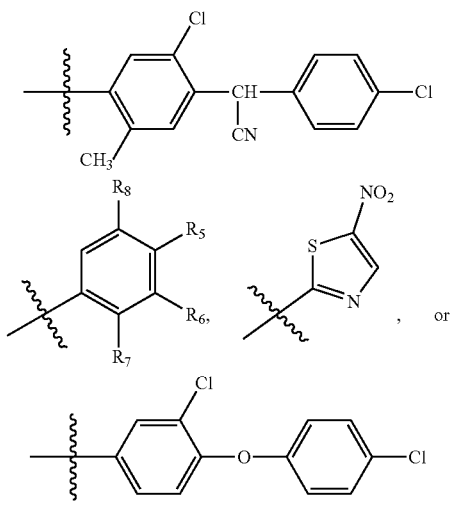

wherein R₅ is —H, —NO₂, or —Br, R₆ is —H, or —Cl; R₇ is —H, or —OH, —Cl; R₈ is —H, or —Cl.

The compounds of Formula-I are salicylamide derivatives. In one embodiment, the compounds of Formula-I include anti-parasitic drugs such as Niclosamide, Oxyclozanide, Rafoxanide, Closantel, Dibromsalan, Metabromsalan, Tribromsalan and Nitazoxanide. In another embodiment, the compounds of Formula-I include anti-parasitic drugs such as Niclosamide, Oxyclozanide, Rafoxanide, Closantel, Dibromsalan, Metabromsalan, and Tribromsalan. It has been found that compounds of formula I are inhibitors of phosphodiesterases and hence may provide safe and effective treatment for PDE related disorders. Accordingly, provided herein is a method for treatment of phosphodiesterase (PDE) related disorders by administering to a subject in need thereof a therapeutically effective amount of compounds of Formula-I, including, for example, anti-parasitic drugs such as Niclosamide, Oxyclozanide, Rafoxanide, Closantel, Dibromsalan, Metabromsalan, Tribromsalan and Nitazoxanide, and their prodrugs, metabolites, or pharmaceutically acceptable salts, solvates and polymorphs thereof in a pharmaceutically acceptable carrier, vehicle, or diluents.

The compounds of Formula-I, or prodrugs or metabolites, or pharmaceutically acceptable salts, solvates and polymorphs thereof, may be administered in a suitable form. The mammal may be a primate, canine, feline, bovine, ovine, porcine, camelid, caprine, rodent or equine. Preferably, the primate is a human.

The PDE related disorders may be treated by administering a therapeutically effective amount of compound of Formula-I, which may include, but is not limited to, Niclosamide, Oxyclozanide, Rafoxanide, Closantel, Dibromsalan, Metabromsalan, Tribromsalan and Nitazoxanide and their prodrugs or metabolites, or pharmaceutically acceptable salts, solvates and polymorphs thereof in a pharmaceutically acceptable carrier, vehicle, or diluents. The administration may be conducted hourly, daily, weekly or monthly. The daily administration may involve anywhere from one to six administrations each day.

The compound of Formula-I may be administered via an oral, intravenous, intraperitoneal, ophthalmic, parenteral, topical, transdermal, subcutaneous, subdural, intravenous, intramuscular, intradermal, intrathecal, intraperitoneal, intracerebral, intraarterial, intralesional, localized or pulmonary route. When administered by oral route, the dosage of the compound of Formula-I is preferably about 1 mg to 3000 mg daily in the form of tablet, capsule, solution, suspension, syrup or dental paste. When administered by ophthalmic route, the dosage of the compound of Formula-I is preferably at a concentration of 0.001% to 10.0% w/v administered 1 to 3 drops (i.e 0.05 mL to 0.15 mL) at each time up to 3 times a day. The ophthalmic composition is administered as eye drops or eye gel. When administered by a topical route, the dosage of the compound of Formula-I is preferably at a concentration of 0.001% to 20.0% w/w applied up to three times a day in a quantity that is sufficient to cover the affected area by the formulation with a layer of approximately 0.1 mm to 5 mm thickness. The topical composition may be in the form of a cream, gel, patch, ointment, topical swab, emulsion, paste, shampoo, solution or spray applied with or without applicator. When administered by intravenous, intradermal, intralesional or subcutaneous route the concentration of therapeutically active ingredient of compound of Formula-I is preferably about 0.001% to 10.0% w/v administered up to 3 times a day with maximum dose of 500 mg each by injection or infusion. The pulmonary composition may be administered to a mammal as an inhaler, nebulizer or vaporizer in a concentration of about 0.001% to 10.0% w/w administered up to 10 times a day.

The present invention further provides a composition and methods of treating PDE related disorders mediated by over-activation of one or more PDE isoforms in a mammal, comprising administering a therapeutically effective amount of compound of Formula-I, a prodrugs or metabolites, or pharmaceutically acceptable salts, solvates and polymorphs thereof to a patient in need thereof. Preferably, the compound of Formula-I is Niclosamide, Oxyclozanide, Rafoxanide, Closantel, Dibromsalan, Metabromsalan, Tribromsalan and Nitazoxanide. The therapeutically effective amount of the compound of Formula-I, prodrug thereof, or pharmaceutically acceptable salt or solvates thereof may be provided in a pharmaceutically acceptable carrier, vehicle or diluent.

Preferably, the PDE related disorders are pulmonary disorders e.g.: asthma, bronchitis, chronic obstructive pulmonary disease (COPD), adult respiratory distress syndrome (ARDS), pulmonary arterial hypertension; allergic diseases such as e.g.: allergic rhinitis and allergic conjunctivitis; endotoxin shock; inflammatory bowel diseases e.g. ulcerative colitis and Crohn's disease; joint disorders such as arthritis, psoriatic arthritis and osteoarthritis; coronary heart disease; intermittent claudication; mental disorders e.g.: dementia, depression, schizophrenia; erectile dysfunction; Duchenne muscular dystrophy; male and female fertility; Dry eye disorder, psoriasis, rosacea, dermatitis; fibrotic skin diseases such as keloids, hypertrophic scarring, collagenoma and systemic sclerosis or scleroderma, Alopecia areata, Lichen Planus, Pemphigus foliaceus, Pemphigus vulgaris, Chronic periodontitis, Dermatitis Herpetiformis, Vitiligo and Bullous Pemphigoid. In some embodiments of this invention, Nitazoxanide in combination with either an antiviral compound or a broad-spectrum antibiotic does not include the treatment of arthritis, osteoarthritis, and bursitis. In some embodiments of this invention, Nitazoxanide alone (i.e., not in combination with either an antiviral compound or a broad-spectrum antibiotic), is administered to a subject in need thereof to treat arthritis, osteoarthritis, and bursitis.

DESCRIPTION OF THE INVENTION

Provided herein are compositions comprising compounds of Formula-I which are antiparasitic drugs, their prodrugs and salts, solvates and polymorphs as well as all possible diastereomers and all enantiomeric forms as well as all combinations of diastereomers and enantiomers, including racemic mixtures and all tautomeric forms.

A subject according to the invention can be any human or animal with PDE related disorders. The animal may be a mammal. The mammal may be a canine, feline, primate, bovine, ovine, porcine, camelia, caprine, rodent, or equine. Preferably, the primate is a human.

In one embodiment, a compound of Formula I is Niclosamide, which, in addition to being an antihelminthic and a piscicide has also been reported as effective in the treatment of neoplasms, protozoal and parasitic infections, acne of bacterial origin, severe acute respiratory syndrome (SARS), Swimmers' itch, as an anti-anthrax toxin, as an anti-neoplastic, and for preventing and/or treating pulmonary fibrosis. In another embodiment, compounds of Formula I are halogenated salicylanilide compounds such as Closantel, Rafoxanide, Oxyclozanide, and Niclosamide, which have been used to treat skin conditions such as impetigo, infected dermatitis (for example infected atopic dermatitis), infected eczema, infected skin wounds, infected burns and infected ulcers (for example diabetic ulcers), originating from bacterial infections arising from Gram-positive bacteria such as *Staphylococcus*, in particular *Staphylococcus aureus*, and *Streptococcus*, in particular *Streptococcus pyogenes*. Oxyclozanide and Rafoxanide are salicylanilides of Formula I which have been used in the treatment and control of Fascioliasis in ruminants. Bromosalans (e.g., Dibromsalan and Tribromsalan) are biphenolic compounds used as fasciolicides effective against juvenile flukes. Brominated derivatives including Dibromsalan, Metabromsalan, and Tribromsalan are used as disinfectants with antibacterial and antifungal activities. Nitazoxanide, a prodrug which upon oral administration, rapidly hydrolyzes to its active metabolite, Tizoxanide, is used for the treatment of infectious diarrhea, illness caused by other protozoa and/or helminths. Nitazoxanide is currently in Phase II clinical trials for the treatment of hepatitis C, in combination with peginterferon alfa-2a and ribavirin. Nitazoxanide alone has shown preliminary evidence of efficacy in the treatment of chronic hepatitis B. Recently, use of Nitazoxanide for treatment of *Mycobacterium tuberculosis* has been proposed. Accordingly, most known compounds of Formula I are generally recognized as anti-infectives (e.g., anti-bacterials, anti-parastics, anti-protozoals). Described herein are methods for re-purposing compounds of Formula I for conditions that are not associated with infections, i.e., PDE related conditions.

The compounds of Formula-I include and are not limited to Niclosamide, Oxyclozanide, Rafoxanide, Closantel, Dibromsalan, Metabromsalan, Tribromsalan and Nitazoxanide, their prodrugs, their metabolites, or pharmaceutically acceptable salts, solvates and polymorphs thereof are surprisingly found to be effective in inhibiting one or more phosphodiesterases like PDE1, PDE2, PDE3, PDE4, PDE5, PDE7, PDE9 and PDE10 and therefore can be utilized for the treatment of PDE related disorders. PDE related disorders associated with elevated PDE activity include and are not limited to pulmonary disorders e.g: asthma, bronchitis, chronic obstructive pulmonary disease (COPD), pulmonary arterial hypertension; allergic diseases e.g: allergic rhinitis and allergic conjunctivitis; endotoxin shock; inflammatory bowel diseases e.g. ulcerative colitis and Crohn's disease; joint disorders such as arthritis, psoriatic arthritis and osteoarthritis; coronary heart disease; intermittent claudication; mental disorders e.g.: dementia, depression, schizophrenia; erectile dysfunction; Duchenne muscular dystrophy; male and female fertility; Dry eye disorder, psoriasis, rosacea, dermatitis; fibrotic skin diseases e.g. keloids, hypertrophic scarring, collagenoma and systemic sclerosis or scleroderma and others. Inhibition of PDE confers a therapeutic effect on PDE-related disorders as shown in the Examples section.

The compounds of formula I are found to inhibit release of several cytokines from Peripheral Blood Mononuclear Cells (PBMCs), in particular Th-17 cytokines like IL-17A, IL-17F and IL22 along with inhibition of cytokine release of IL-12 (See Example 5). These cytokines are among PDE regulated downstream cytokines. Considering this effective inhibition of Th-17 cytokines, the compounds of formula I can be utilized for treatment of several diseases like Alopecia areata, Lichen Planus, Pemphigus foliaceus, Pemphigus vulgaris, chronic periodontitis, Dermatitis Herpetiformis, Vitiligo and Bullous Pemphigoid.

An embodiment of this invention includes compositions of compounds having the structure of Formula-I for treating phosphodiesterase related disorders in a mammal,

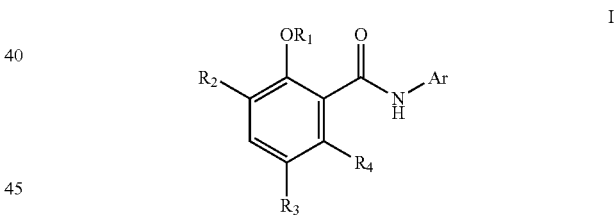

wherein R1 is —H or —COCH$_3$; R$_2$ is —H, —Cl, —Br, or —I; R$_3$ is —H, —Cl, —Br, or —I; R$_4$ is —H, or —Cl; Ar is

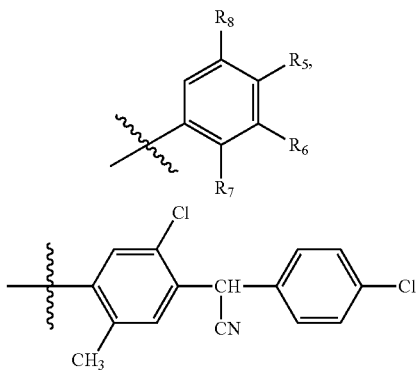

-continued

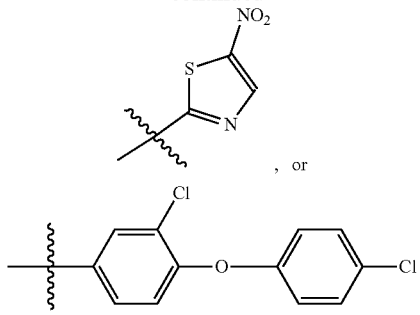

, or wherein $R_5$ is —H, —$NO_2$, or —Br, $R_6$ is —H, or —Cl; $R_7$ is —H, or —OH, —Cl; $R_8$ is —H, or —Cl.

Also an embodiment of this invention is a method of treating phosphodiesterase related disorders in a mammal, comprising administering a therapeutically effective amount of a composition comprising a compound of Formula-I, or a prodrug or a metabolite thereof, or pharmaceutically acceptable salts, solvates and polymorphs thereof in a pharmaceutically acceptable carrier, vehicle, or diluents to a subject in need of such treatment.

In an aspect, provided is a method for inhibiting a phosphodiesterase, comprising contacting a phosphodiesterase with a compound of formula-I

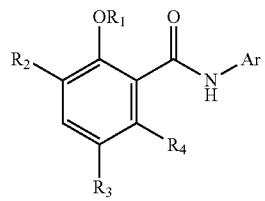

I wherein $R_1$ is —H or —$COCH_3$; $R_2$ is —H, —Cl, —Br, or —I; $R_3$ is —H, —Cl, —Br, or —I; $R_4$ is —H, or —Cl; Ar is

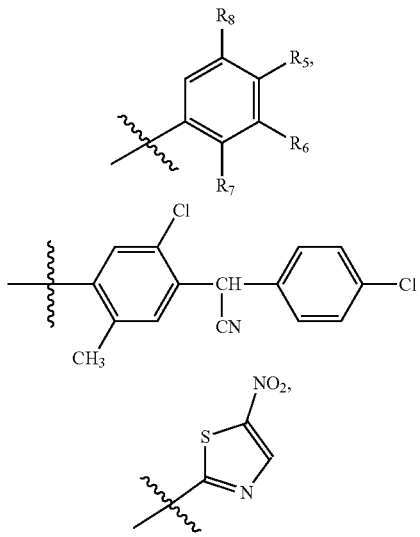

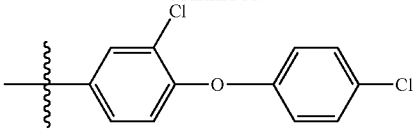

wherein $R_5$ is —H, —$NO_2$, or —Br,
$R_6$ is —H, or —Cl; $R_7$ is —H, —OH, or —Cl; $R_8$ is —H, or —Cl; and enantiomers, diastereomers, prodrugs or metabolites thereof, or pharmaceutically acceptable salts, solvates and polymorphs thereof.

Definitions

The term "therapeutically effective amount" refers to the amount required for reduction in the severity of symptoms of the PDE related disorders.

Psoriasis may include types of psoriasis like Plaque psoriasis (psoriasis vulgaris), Guttate psoriasis, Inverse psoriasis, Erythrodermic psoriasis and Pustular Psoriasis. The psoriasis may be expressed at one or more body organs simultaneously including scalp.

Dermatitis may include various types of dermatitis like atopic dermatitis, contact dermatitis, stasis dermatitis, Dyshidrotic Dermatitis, Nummular Dermatitis, Neurodermatitis and Seborrheic Dermatitis.

Rosacea may include Erythematotelangiectatic Rosacea, Papulopustular Rosacea, Phymatous Rosacea and Ocular Rosacea.

Methods of Administration

One aspect of the disclosure contemplates the use of therapeutically effective amount of anti-parasitic drugs of Formula-I such as Niclosamide, Oxyclozanide, Rafoxanide, Closantel, Dibromsalan, Metabromsalan, Tribromsalan and Nitazoxanide, their prodrugs, their metabolites, or pharmaceutically acceptable salts, solvates and polymorphs thereof in the treatment of PDE related disorders, including pulmonary disorders e.g: asthma, bronchitis, chronic obstructive pulmonary disease (COPD), pulmonary arterial hypertension; allergic diseases e.g.: allergic rhinitis and allergic conjunctivitis; endotoxin shock; inflammatory bowel diseases e.g. ulcerative colitis and Crohn's disease; joint disorders such as arthritis, psoriatic arthritis and osteoarthritis; coronary heart disease; intermittent claudication; mental disorders e.g.: dementia, depression, schizophrenia; erectile dysfunction; Duchenne muscular dystrophy; male and female fertility; Dry eye disorder, psoriasis, rosacea, dermatitis; fibrotic skin diseases e.g. keloids, hypertrophic scarring, collagenoma and scleroderma; Alopecia areata, Lichen Planus, Pemphigus foliaceus, Pemphigus vulgaris, chronic periodontitis, Dermatitis Herpetiformis, Vitiligo and Bullous Pemphigoid. The compounds of Formula-I have been found to treat PDE related disorders by inhibiting PDEs and various downstream mechanisms, including, but not limited to, inhibiting release of cytokines and chemokines; inhibiting release of one or many markers of inflammation such as TNF-α, STAT3, NFκB, and combinations thereof.

The anti-parasitic drugs of Formula-I such as Niclosamide, Oxyclozanide, Rafoxanide, Closantel, Dibromsalan, Metabromsalan, Tribromsalan and Nitazoxanide, their prodrugs, their metabolites, and salts, solvates and polymorphs thereof intended for PDE related disorders are administered in a physiologically acceptable carrier to a subject. The treatment of some of the PDE related disorders may be administered in a variety of ways including but not limited to oral administration, ophthalmic administration, nasal administration, parenteral administration, including topical, local dermal as well as transdermal, subcutaneous (s.c.), subdural, intravenous (i.v.), intramuscular (i.m.), intradermal intrathecal, intraperitoneal (i.p.), intracerebral, intra-arterial, or intralesional routes of administration, localized (e.g., surgical application or surgical suppository), and pulmonary (e.g., aerosols, inhalation, or powder) and as described further below.

The correct dosage of a pharmaceutical composition comprising anti-parasitic drugs of Formula I will vary according to the pharmaceutical formulation, the mode of application, as well as the particular site, host and PDE related disorder being treated. Other factors including age, body weight, sex, diet, time of administration, rate of excretion, condition of the host, drug combinations, reaction sensitivities and severity of the disease may be readily taken into account by a treating professional or one of skill in the art. The dosage of the claimed compounds depends on several factors, including: the administration method, the disease to be treated, the severity of the disease, whether the disease is to be treated or prevented.

Administration may be carried out continuously or periodically within the maximum tolerated dose. The administration may be conducted, for example, hourly, once every two hours, once every three hours, once every six hours, once every eight hours, once every twelve hours, daily, alternate day, weekly, every two weeks, every three weeks, or monthly, as needed. The dose may be administered from one day to 12 months depending on disease or condition to be treated or prevented.

The topical route of administration is a preferred route for treatment of skin diseases like psoriasis, rosacea, dermatitis and fibrotic diseases such as keloids, hypertrophic scarring, collagenoma and scleroderma as well as diseases like Alopecia areata, Lichen Planus, Pemphigus foliaceus, Pemphigus vulgaris, chronic periodontitis, Dermatitis Herpetiformis, Vitiligo and Bullous Pemphigoid. The topical dermal composition comprising anti-parasitic drugs of Formula I acts locally and penetrate to skin layers like stratum corneum, other parts of epidermis and parts of dermis. The topical pharmaceutical composition comprising anti-parasitic drugs of Formula I exclude water resistant, anti-penetrant topical formulation. Suitable compositions for topical administration may include creams, gels, lotions, soaps, shampoos, aerosol, balm, serum, mousse, patch, paste, pump spray, roll-on, topical solution, stick, towelette, ointment, wipe, emulsion, cosmetic, and any combination thereof. In the treatment of skin diseases, compounds of Formula I of present invention have been found to be useful. Thus, the present invention provides a pharmaceutical composition for topical administration, for the treatment of skin diseases like psoriasis, rosacea, dermatitis and fibrotic skin diseases as well as diseases like Alopecia areata, Lichen Planus, Pemphigus foliaceus, Pemphigus vulgaris, chronic periodontitis, Dermatitis Herpetiformis, Vitiligo and Bullous Pemphigoid, comprising anti-parasitic drugs of present invention, prodrugs thereof, or a pharmaceutically acceptable salt or solvates thereof, in a pharmaceutically acceptable topical carrier, vehicle, or diluent. The topical composition comprising compound of Formula-I of present invention is preferably in the form of a gel, a patch, topical solution, cream, ointment, topical swab, emulsion, shampoo, spray or lotion. The composition may be provided in sustained release form.

Depending upon the manner of administration, the anti-parasitic drugs of Formula-I of present invention, their prodrugs or metabolites, or pharmaceutically acceptable salts, solvates and polymorphs may be formulated in various ways. The concentration of the compound of Formula-I in a formulation for topical administration may vary from a concentration of about 0.001% to 20.0% w/w administered one to ten times daily for one week to 12 months is usually preferable. Preferably, the concentration of the anti-parasitic drugs in a formulation for topical administration may vary from a concentration of about 0.001% to 10.0% w/w. In treating skin diseases like psoriasis, rosacea, dermatitis and fibrotic skin diseases, a composition containing compound of Formula-I of present invention as the active ingredient may be advantageously administered to subject in need by way of a topical preparation, having a concentration of anti-parasitic drugs of present invention of about 0.001% to 10.0% w/w in a suitable pharmaceutical carrier. In treating pulmonary diseases, the anti-parasitic drug may be administered to a mammal as an inhaler, nebulizer or vaporizer in a concentration of about 0.001% to 10.0% w/w and preferably of 0.1% to 5% w/w for one to ten times a day for one day to 12 months or more.

When administered by oral route, the dosage of the anti-parasitic drug of present invention is preferably about 0.1 mg to 3000 mg daily (desirably about 0.5 mg to 2000 mg) one to ten times daily (preferably one to five times daily, more desirably one to three times daily) for period of one day to 12 months or more. When administered by ophthalmic route, the dosage of the anti-parasitic drug of present invention is preferably at a concentration of 0.001% to 10.0% w/v administered one to ten drops i.e. 0.05 mL to 0.5 mL (preferably one to three drops i.e. 0.05 mL to 0.15 mL) at each time up to ten times a day (preferably one to five times daily, more desirably one to three times daily) for period of one day to 12 months or more. When administered by a topical route, the dosage of the anti-parasitic drug of present invention is preferably at a concentration of 0.001% to 20.0% w/w applied one to ten times a day for period of one week to 12 months or more in a quantity that is sufficient to cover the affected area by the formulation with a layer of approximately 0.1 mm to 5 mm thickness. When administered by intravenous or intramuscular route, the concentration of therapeutically active ingredient of anti-parasitic drug of present invention is preferably about 0.001% to 10.0% w/v administered one to ten times a day with maximum dose of 500 mg per application for period of one day to 12 months or more.

Preferably, the anti-parasitic drugs of present invention, their prodrugs, or pharmaceutically acceptable salts, solvates and polymorphs, the concentration of such therapeutically active ingredient in a formulation for oral administration may vary from a concentration of about 1 mg to 3000 mg daily for any of the PDE-related disorders. The concentration of the anti-parasitic drugs of present invention in a formulation for ophthalmic administration may vary from a concentration of about 0.001% to 10.0% w/v. The concentration of therapeutically active ingredient of anti-parasitic drugs of present invention in a formulation for intravenous, intradermal, intralesional or intramuscular administration may vary from a concentration of about 0.001% to 10.0% w/v.

For parenteral administration, anti-parasitic drugs of present invention, their prodrugs, or pharmaceutically acceptable salts, solvates and polymorphs of the invention can be administered as injectable dosages of a solution or suspension of the substance in a physiologically acceptable diluent with a pharmaceutical carrier, which can be a sterile liquid such as water and oils with or without the addition of a surfactant. Other acceptable diluents include oils of animal, vegetable, or synthetic origin, for example, peanut oil, soybean oil, and mineral oil. In general, glycols such as propylene glycol or polyethylene glycol (PEG) are preferred liquid carriers, particularly for injectable solutions. The anti-parasitic drugs of present invention, their prodrugs, or pharmaceutically acceptable salts, solvates and polymorphs of this disclosure can be administered in the form of a depot injection or implant preparation, which can be formulated in such a manner as to permit a controlled or sustained release of the active ingredient(s).

Pharmaceutical compositions comprising anti-parasitic drugs of present invention, their prodrugs, or pharmaceutically acceptable salts, solvates and polymorphs may also include pharmaceutically acceptable, non-toxic carriers or diluents, which are vehicles commonly used to formulate pharmaceutical compositions for animal or human administration. The formulations may also contain conventional additives, such as solubilizers, isotonic agents, suspending agents, emulsifying agents, stabilizers, penetrating agents, humectant and preservatives.

The compositions may be formulated for sustained release. The anti-parasitic drugs of present invention, their prodrugs, or pharmaceutically acceptable salts, solvates and polymorphs of this invention can be administered in a sustained release form, for example a depot injection, implant preparation, or osmotic pump, which can be formulated in such a manner as to permit a sustained release of the active ingredient. Implants for sustained release formulations are well-known in the art. Implants are formulated as microspheres, slabs, etc. with biodegradable or non-biodegradable polymers. For example, polymers of lactic acid and/or glycolic acid form an erodible polymer that are well-tolerated by the host.

Example 1: Computational Model(s) Prediction of Anti-Parasitic Drug Niclosamide to be a Potent Phosphodiesterase Inhibitor The screening of small molecule database using in-silico docking techniques suggested drug Niclosamide to be a potent candidate for PDE inhibition. GRIP docking of Niclosamide along with ligand flexibility with the aim of exploring the conformational space of the molecule, was done in various PDE isotype crystal structures, as provided in VlifeMDS software (VLifeMDS version 4.1: Molecular Design Suite developed by NovaLead Pharma Pvt. Ltd., Pune, India 2014. In PDE4B (1RO6), docking pose confirms the possibility of Niclosamide binding to phosphodiesterase mainly by two hydrogen bonds with Thr407, Gln443 and pi-stacking interactions with Phe446 and Phe414. These interactions are common with many of the co-crystallized ligands for PDE4B structures. Similarly, Niclosamide docked in to various crystal structures of PDE4D and PDE10A showed promising binding in the corresponding active site. Thus, Niclosamide has shown ability to bind to one or more isotypes of PDEs and hence can be promising PDE inhibitor. The other anti-parasitic drugs of Formula-I have structural similarity (similarity index) with Niclosamide as provided below in Table I:

TABLE I

Similarity index of drugs w.r.t Niclosamide

| Drug Name | Similarity Index |
| --- | --- |
| Dibromsalan | 0.68 |
| Tribromsalan | 0.67 |
| Metabromsalan | 0.50 |
| Rafoxanide | 0.75 |
| Oxyclozanide | 0.76 |
| Closantel | 0.70 |
| Nitazoxanide | 0.52 |
| Niclosamide | 1.0 |

The high structural similarity indicates that these drugs (compounds of Formula-I) bind to one or more isoenzymes of PDE in a similar fashion to that of Niclosamide and hence also are PDE inhibitors.

All other anti-parasitic drugs of Formula-I such as Nitazoxanide, Oxyclozanide, Rafoxanide, Dibromsalan, Metabromsalan, and Tribromsalan were docked in various crystal structures of PDE isoenzymes. These drugs are found to bind effectively to one or more PDE isoenzyme structures. The information about a representative enzyme interacting with anti-parasitic drugs of present invention along with their key interactions similar to those with corresponding co-crystallized ligands is summarized below in the Table-II below.

TABLE II

Docking interactions of drugs with PDEs

| Drug involved | PDE type | PDB code | H-bonding residues | Pi-stacking residues |
| --- | --- | --- | --- | --- |
| Niclosamide | PDE4B | 1RO6 | Thr407, Gln443 | Phe446, Phe414 |
|  | PDE4D | 3SL4 | Gln369 | Phe372, Phe340 |
|  | PDE10A | 4DFF | Gln726 | Phe729 |
| Nitazoxanide | PDE4B | 1XM6 | Gln443 | Phe446, Phe414, Tyr233 |
|  | PDE4A | 3I8V | Gln581, Tyr371 | Phe584, Tyr371, His372, His376 |
|  | PDE10A | 4AEL | Gln726 | Phe729, Phe696 |
| Dibromsalan | PDE4D | 1Y2C | Gln369 | Phe372, Phe340 |
|  | PDE10A | 3UUO | Gln726 | Phe729, Phe696 |
| Oxyclozanide | PDE4A | 3I8V | Tyr371 | Phe584 |
|  | PDE10A | 3UUO | Gln726 | Phe729, Phe696, Tyr524 |
|  | PDE5 | 2H44 | Gln817 | Phe820, Phe786, Tyr612 |
| Rafoxanide | PDE7A | 1ZKL | Asn260 | Phe416 |
|  | PDE10A | 4AEL | Gln726 | Phe729, Phe696 |
| Metabromsalan | PDE4B | 1RO6 | Gln443 | Phe446, Phe414 |
|  | PDE4A | 2QYK | Gln581 | Phe584, Tyr371, Phe552 |

TABLE II-continued

Docking interactions of drugs with PDEs

| Drug involved | PDE type | PDB code | H-bonding residues | Pi-stacking residues |
|---|---|---|---|---|
| Tribromsalan | PDE5A | 3TGE | Gln817 | Phe820, Phe786, Tyr612 |
| | PDE4B | 1RO6 | Gln443 | Phe446 |
| Closantel | PDE4A | 3I8V | His372 | Tyr371, Phe584 |
| | PDE7A | 1ZKL | Asn260 | Tyr419 |
| | PDE4D | 3SL4 | Asn209, Gln343, Ser355 | Phe372 |

The above results indicated that anti-parasitic drugs of present invention (compounds of Formula-I) have potential to bind and inhibit one or more types of PDE isomers.

Example 2: Evaluation of Phosphodiesterase Inhibition Action of Niclosamide and Nitazoxanide in Radiolabeled Enzyme Assay The following enzymes were utilized to check PDE inhibitory activity of Niclosamide and Nitazoxanide: PDE1 (Bovine brain), PDE2 (Human platelets), PDE3 (Human platelets), PDE4 (Human U937 cells), PDE5 (Human platelets). Enzyme assays have been optimized for incubation time, substrate concentration and method of end-product determination. The substrate used for PDE1 to PDE4 are 1.01 µM [$^3$H] cAMP+cAMP; whereas for PDE5 it is 1.01 µM [$^3$H] cGMP+cGMP.

The results of % inhibition of various isotypes of PDE by Niclosamide and Nitazoxanide are given below in Table III:

TABLE III

PDE inhibition of Niclosamide and Nitazoxanide in radiolabeled enzyme assay

| S. No. | Phosphodiesterase Type | % inhibition at 30 µM of Niclosamide | % inhibition at 30 µM of Nitazoxanide |
|---|---|---|---|
| 1 | PDE1 | 61 | 18 |
| 2 | PDE2 | 16 | 13 |
| 3 | PDE3 | 62 | −4 |
| 4 | PDE4 | 27 | 89 |
| 5 | PDE5 | 49 | 9 |

The above data shows that Niclosamide has good ability to inhibit many PDE isotypes. The binding of Niclosamide with PDE isotypes was further confirmed in experiments and detailed studies. IC50 values of Niclosamide were determined for PDE3 and PDE1, which were found to be 21.3 µM and 72.9 µM respectively. The data shows that Niclosamide has inhibitory activity against multiple PDEs. The above data also shows that Nitazoxanide has PDE4 inhibitory activity.

Example 3: In-Vitro Evaluation of PDE Inhibition of Drugs by Fluorescence Polarization Assay An experiment to check inhibition of various subtypes of the target Phosphodiesterase (PDE) enzyme in in-vitro assay was performed. The in-vitro experiment determined the IC50 values of Niclosamide, Nitazoxanide and Tizoxanide in 10 PDE subtypes viz. PDE1A, PDE2A, PDE4A, PDE4B, PDE4C, PDE4D, PDE5A, PDE7A, PDE9A, PDE10A.

The result of IC50 of three drugs against various PDE subtypes is given in Table IV

TABLE IV

IC50 values of Niclosamide, Nitazoxanide and Tizoxanide for PDE subtypes.

| PDE Enzyme | Substrate | IC50 (µM) | | |
|---|---|---|---|---|
| | | Niclosamide | Nitazoxanide | Tizoxanide |
| PDE1A | cGMP, Ca-CaM | 88.66 | 137 | 96.1 |
| PDE2A | cGMP | 11.59 | 67.5 | 12.0 |
| PDE4A | cAMP | 100.00 | — | — |
| PDE4B | cAMP | 69.06 | >500 | >500 |
| PDE4C | cAMP | 20.22 | — | 366.0 |
| PDE4D | cAMP | 111.20 | — | — |
| PDE5A | cGMP | 16.70 | — | 136.0 |
| PDE7A | cAMP | 19.12 | — | 134.0 |
| PDE9A | cGMP | 59.82 | — | — |
| PDE10A | cAMP | 19.05 | — | — |

The data shows that Niclosamide, Nitazoxanide and Tizoxanide inhibit one or more PDE subtypes. Niclosamide is a non-selective inhibitor of PDE whereas Nitazoxanide and its metabolite Tizoxanide show inhibition of PDE2A and PDE A.

Example 4: In-Vitro Evaluation of Inhibition of Keratinocyte (HaCat) Proliferation An experiment to check keratinocyte proliferation inhibitory activity of selected compounds of Formula-I was performed to establish its application in skin disorders related to keratinocyte hyper-proliferation. HaCaT cells, a human immortalized cell line derived from keratinocytes, representing hyper-proliferating keratinocytes was investigated for anti-proliferative potential of the selected compounds by MTT assay.

The results of % Cell proliferation w.r.t. control for Niclosamide, Nitazoxanide and Tizoxanide at 24 h, 48 h and 72 h are given in Table V:

TABLE V

Inhibition of cell proliferation w.r.t. control at 24, 48 and 72 hrs for Niclosamide, Nitazoxanide and Tizoxanide

| Compound | Concentration µM | Cell proliferation (% of Control) | | |
|---|---|---|---|---|
| | | 24 h | 48 h | 72 h |
| Niclosamide | Control | 100 | 100 | 100 |
| | 0.01 | 129.5 | 124.8 | 109.5 |
| | 0.1 | 114.5 | 103.8 | 94 |
| | 0.5 | 121.5 | 70.5 | 66.5 |
| | 1 | 94.8 | 55 | 60.4 |
| | 2.5 | 94.8 | 57.9 | 55 |

TABLE V-continued

Inhibition of cell proliferation w.r.t. control at 24, 48 and 72 hrs for Niclosamide, Nitazoxanide and Tizoxanide

|  |  | Cell proliferation (% of Control) | | |
|---|---|---|---|---|
| Compound | Concentration µM | 24 h | 48 h | 72 h |
|  | 5 | 96.7 | 62 | 40.7 |
|  | 10 | 107.4 | 64.1 | 39.2 |
|  | 25 | 115.4 | 74.6 | 37.6 |
|  | IC$_{50}$ | NA | NA | 3.25 uM |
| Nitazoxanide | Control | 100 | 100 | 100 |
|  | 0.01 | 126.3 | 113.7 | 114.6 |
|  | 0.1 | 114.3 | 115.2 | 102.4 |
|  | 0.5 | 120.3 | 113.4 | 106.2 |
|  | 1 | 123 | 110.8 | 101.7 |
|  | 5 | 121.6 | 91.8 | 82.9 |
|  | 10 | 103.8 | 77 | 69.5 |
|  | 50 | 92.6 | 69.6 | 49.6 |
|  | 100 | 89.7 | 61 | 33.1 |
|  | IC$_{50}$ | NA | NA | 39.94 uM |
| Tizoxanide | Control | 100 | 100 | 100 |
|  | 0.01 | 98.2 | 109.5 | 87.4 |
|  | 0.1 | 93.9 | 120.1 | 82.7 |
|  | 0.5 | 93.2 | 108.9 | 87.7 |
|  | 1 | 99.7 | 112.4 | 81 |
|  | 5 | 101.6 | 89.3 | 77.9 |
|  | 10 | 94.9 | 74.1 | 64.3 |
|  | 50 | 67.3 | 59.9 | 38 |
|  | 100 | 53.5 | 38.6 | 22.8 |
|  | IC$_{50}$ | NA | 59.89 uM | 22.35 uM |

The above data shows that Niclosamide, Nitazoxanide and Tizoxanide have good ability to inhibit keratinocyte proliferation after 48 Hrs. This clearly indicates that compounds of Formula-I of present invention have a promise in one or more skin diseases involving keratinocyte hyperproliferation.

Example 5: In-Vitro Evaluation of Drugs on Cell Viability and Cytokine Production in Human PBMCs Fresh human blood from healthy volunteer was collected in anticoagulant (5 mM) ethylene diamine tetra acetic acid (EDTA) containing tubes. The growth medium used was RPMI-1640 medium (with 3% FBS) and incubated at 37'C for 60 mins in a 5% CO2 incubator with vehicle used as 1% DMSO. The cell viability was checked at various time points using Alamar blue and fluorescence readings were taken at excitation of 544 nm and emission of 590 nm.

Results:

The results of % Cell viability w.r.t. control for Niclosamide, Nitazoxanide and Tizoxanide at 24 h, 48 h and 72 h are given in Table VI:

TABLE VI

% Cell viability of PBMCs in presence of drugs at various concentrations and at various time points

| Compound | Concentration (µM) | % Viability (±S.E.M.) | | |
|---|---|---|---|---|
|  |  | 24 hrs | 48 hrs | 72 hrs |
| DMSO control | — | 100 ± 0 | 100 ± 1 | 100 ± 4 |
| Dexamethasone | 3 | 82 ± 6 | 78 ± 1 | 81 ± 1 |
| Doxorubicin | 3 | 110 ± 1 | 70 ± 5 | 52 ± 1 |
| Niclosamide | 100 | 27 ± 5 | 2 ± 1 | -2 ± 0 |
|  | 1 | 94 ± 4 | 63 ± 0 | 60 ± 1 |
|  | 0.01 | 134 ± 7 | 107 ± 1 | 107 ± 6 |
| Nitazoxanide | 100 | 76 ± 4 | 42 ± 4 | 11 ± 3 |
|  | 1 | 91 ± 2 | 105 ± 7 | 106 ± 2 |
|  | 0.01 | 97 ± 1 | 106 ± 8 | 113 ± 10 |
| Tizoxanide | 100 | 91 ± 5 | 64 ± 2 | 25 ± 2 |
|  | 1 | 84 ± 2 | 101 ± 4 | 102 ± 3 |
|  | 0.01 | 91 ± 3 | 96 ± 3 | 115 ± 1 |

The concentration of selected compounds of Formula-I, which exhibited cell viability of 70% was considered as maximum concentration at which the stimulation of PBMCs should be studied for the respective compound. This was found to be 2.5 µM for Niclosamide and 50 uM for Nitazoxanide and Tizoxanide, hence concentrations below this concentration were used to study various cytokine inhibition/induction upon stimulation of PBMCs. All measurements were done in triplicate.

Stimulants Used:

PBMCs were stimulated with different stimulators as follows:

a. Cells were exposed to stimulator LPS at 100 ng/mL for 18 hrs to stimulate TNF-α, IL-6, IFN-γ, IL10, IL-1β
b. Cells were exposed to stimulator IFN-γ+LPS at 100 ng/mL+1 µg/mL for 18 hrs to stimulate IL-12
c. Cells were exposed to stimulator PMA+Ionomycin at 50 ng/mL+1 µg/mL for 18 hrs to stimulate IL-23, IL-22, IL-17A, IL-17F After 18 hrs supernatants were collected and centrifuged to remove any cell debris and aliquots were used for ELISA.

Results

Effect of selected compounds of Formula-I on induction/inhibition of inflammatory cytokines in stimulated PBMCs is shown below.

TABLE VII

Cytokine concentration in (pg/mL) in presence of stimulus and various drug concentrations

| | Conc (µM) | Human IL-22 | Human IL-17A | Human IL-17F | Human TNF-α | Human IL-6 | Human IL-10 | Human IL-12 | Human IFN-γ | Human IL-1β |
|---|---|---|---|---|---|---|---|---|---|---|
| Cells + 0.5% DMSO | — | 0 ± 0 | 0 ± 0 | 0 ± 0 | 65 ± 3 | 1471 ± 47 | 128 ± 0 | 114 ± 0 | 178 ± 13 | 903 ± 30 |
| Cells + 0.5% DMSO + Stimulus* | — | 9421 ± 848 | 381 ± 0 | 364 ± 16 | 3296 ± 193 | 5568 ± 781 | 1222 ± 47 | 4351 ± 237 | 204 ± 13 | 2138 ± 99 |
| Dexamethasone | 1 | 2496 ± 34 | 186 ± 0 | 322 ± 10 | 325 ± 7 | 3052 ± 221 | 710 ± 21 | 163 ± 0 | 165 ± 0 | 174 ± 0 |
| Niclosamide | 2.5 | 84 ± 0 | 0 ± 0 | 0 ± 0 | 3074 ± 91 | 3103 ± 75 | 53 ± 0 | 138 ± 0 | 165 ± 26 | 2166 ± 31 |

TABLE VII-continued

Cytokine concentration in (pg/mL) in presence of stimulus and various drug concentrations

|  | Conc (μM) | Human IL-22 | Human IL-17A | Human IL-17F | Human TNF-α | Human IL-6 | Human IL-10 | Human IL-12 | Human IFN-γ | Human IL-1β |
|---|---|---|---|---|---|---|---|---|---|---|
|  | 1 | 756 ± 16 | 0 ± 0 | 0 ± 0 | 2938 ± 15 | 4435 ± 245 | 89 ± 13 | 663 ± 12 | 125 ± 14 | 4519 ± 1373 |
|  | 0.5 | 2795 ± 195 | 0 ± 0 | 0 ± 0 | 3839 ± 73 | 5653 ± 697 | 837 ± 65 | 1359 ± 0 | 125 ± 14 | 4126 ± 596 |
|  | 0.1 | 10574 ± 0 | 350 ± 32 | 202 ± 2 | 4611 ± 150 | 5682 ± 668 | 1645 ± 180 | 1221 ± 0 | 165 ± 26 | 4287 ± 959 |
| Nitazoxanide | 50 | 0 ± 0 | 0 ± 0 | 0 ± 0 | 2896 ± 117 | 2531 ± 94 | 42 ± 11 | 101 ± 12 | 191 ± 0 | 2506 ± 139 |
|  | 25 | 228 ± 0 | 0 ± 0 | 0 ± 0 | 3679 ± 123 | 3567 ± 127 | 76 ± 0 | 406 ± 0 | 152 ± 13 | 3203 ± 326 |
|  | 10 | 1093 ± 6 | 0 ± 0 | 0 ± 0 | 3472 ± 50 | 5342 ± 386 | 512 ± 19 | 1500 ± 29 | 125 ± 14 | 3971 ± 217 |
|  | 1 | 5612 ± 373 | 39 ± 0 | 166 ± 10 | 5708 ± 27 | 5520 ± 506 | 1799 ± 79 | 3892 ± 88 | 217 ± 0 | 4470 ± 636 |
| Tizoxanide | 50 | 0 ± 0 | 0 ± 0 | 0 ± 0 | 2440 ± 13 | 2086 ± 38 | 42 ± 11 | 101 ± 12 | 191 ± 0 | 2522 ± 80 |
|  | 25 | 280 ± 0 | 0 ± 0 | 0 ± 0 | 3489 ± 34 | 3428 ± 154 | 76 ± 0 | 381 ± 0 | 139 ± 0 | 4168 ± 1079 |
|  | 10 | 1189 ± 18 | 0 ± 0 | 0 ± 0 | 3244 ± 48 | 5225 ± 649 | 493 ± 0 | 4101 ± 42 | 111 ± 0 | 4118 ± 853 |
|  | 1 | 7858 ± 1361 | 39 ± 0 | 151 ± 5 | 5351 ± 174 | 6122 ± 865 | 1591 ± 25 | 4715 ± 176 | 204 ± 13 | 4577 ± 975 |

*Stimulus and its concentration for each cytokine release as per information above

* Stimulus and its concentration for each cytokine release as per information above Inferences drawn from above table are:
1. Cytokine assays stimulated with LPS or LPS+ IFN-γ: All the tested compounds appear to show robust and dose dependent inhibition of IL-12 and IL-10, moderate inhibition of IL-6, little or no effect on TNF-α, IFN-γ, and IL-1β.
2. Cytokine assays stimulated with PMA+Ionomycin: All the tested compounds appear to show robust inhibition of Th17-type cytokines IL-17A, IL-17F and IL-22. PMA+Ionomycin did not induce IL-23.

Example 6: In-Vitro Evaluation of Drugs on Cell Viability and Cytokine Production in HaCaT Cells HaCaT cells were maintained in T-75 cm2 flask in Dulbecco's modified Eagle medium supplemented with FBS (10%), L-glutamine (2 mM), penicillin (100 ug/ml), streptomycin (100 ug/ml) at 37° C. in 5% CO2 incubator. Cell growth was maintained to 70-80% confluence for seeding and vehicle used was 1% DMSO. The cell viability was checked at various time points using Alamar blue and fluorescence readings were taken at excitation of 544 nm and emission of 590 nm.

Results:
The results of % Cell viability w.r.t. control for Niclosamide, Nitazoxanide and Tizoxanideat 24 h, 48 h and 72 h are given in Table VIII:

TABLE VIII

% Cell viability of HaCaT in presence of drugs at various concentrations and at various time points

|  |  | % Viability (± S.E.M.) | | |
|---|---|---|---|---|
| Compound | Conc (μM) | 24 hrs | 48 hrs | 72 hrs |
| DMSO control | — | 100 ± 11 | 100 ± 2 | 100 ± 2 |
| Dexamethasone | 3 | 46 ± 3 | 18 ± 2 | 8 ± 0 |
| Doxorubicin | 3 | 74 ± 6 | 108 ± 5 | 110 ± 2 |
| Niclosamide | 50 | 28 ± 1 | 16 ± 0 | 23 ± 7 |
|  | 10 | 38 ± 2 | 29 ± 1 | 33 ± 2 |
|  | 5 | 48 ± 1 | 36 ± 2 | 45 ± 8 |
|  | 1 | 62 ± 4 | 46 ± 0 | 59 ± 11 |
|  | 0.1 | 111 ± 9 | 82 ± 3 | 98 ± 6 |
| Nitazoxanide | 100 | 17 ± 1 | 13 ± 1 | 17 ± 1 |
|  | 50 | 18 ± 1 | 15 ± 2 | 18 ± 1 |
|  | 10 | 41 ± 1 | 40 ± 2 | 46 ± 3 |
|  | 1 | 81 ± 3 | 86 ± 8 | 91 ± 2 |
|  | 0.1 | 89 ± 1 | 99 ± 9 | 103 ± 3 |

TABLE VIII-continued

% Cell viability of HaCaT in presence of drugs at various concentrations and at various time points

|  |  | % Viability (± S.E.M.) | | |
|---|---|---|---|---|
| Compound | Conc (μM) | 24 hrs | 48 hrs | 72 hrs |
| Tizoxanide | 100 | 20 ± 0 | 13 ± 0 | 20 ± 0 |
|  | 50 | 24 ± 1 | 20 ± 0 | 25 ± 0 |
|  | 10 | 34 ± 1 | 35 ± 0 | 43 ± 1 |
|  | 1 | 74 ± 6 | 91 ± 5 | 91 ± 2 |
|  | 0.1 | 76 ± 6 | 114 ± 2 | 112 ± 6 |

The concentration of compounds of Formula-I which exhibited cell viability of 70% was considered as maximum concentration at which the stimulation of HaCaT cells should be studied. This was found to be 0.25 μM for Niclosamide, 1 uM for Nitazoxanide and Tizoxanide, and hence concentrations below this concentration were used to study various cytokine inhibition/induction upon stimulation of HaCaT cells. All measurements were done in triplicate.

Stimulants Used:
HaCaT cells were stimulated with different stimulators as follows:
a. Cells were exposed to stimulator LPS at 1 μg/mL for 48 hrs to stimulate IL-1β
b. Cells were exposed to stimulator IFN-γ at 50 ng/mL for 48 hrs to stimulate TNF-α, IL-6

After 48 hrs supernatants were collected and centrifuged to remove any cell debris and aliquots were used for ELISA.

Results
Effect of compounds of Formula-I on induction/inhibition of inflammatory cytokines in stimulated HaCaT cells is shown in Table IX.

TABLE IX

Cytokine concentration in (pg/mL) in presence of stimulus and various drug concentrations

|  |  | TNF-α | IL-6 |
|---|---|---|---|
| Group | Conc. (μM) | Conc. (pg/mL) | |
| DMSO | 0.50% | 2.8 ± 0.1 | 17 ± 1 |
| Control (0.5% DMSO + Stimulus) |  | 3.3 ± 0.1 | 82 ± 1 |
| Dexamethasone | 1 | 3.2 ± 0 | 33 ± 1 |
| Niclosamide + Stimulus | 0.25 | 2.5 ± 0.1 | 54 ± 11 |
|  | 0.1 | 2.8 ± 0.1 | 76 ± 4 |
|  | 0.05 | 2.5 ± 0.1 | 103 ± 4 |

TABLE IX-continued

Cytokine concentration in (pg/mL) in presence of stimulus and various drug concentrations

| Group | Conc. (μM) | TNF-α Conc. (pg/mL) | IL-6 Conc. (pg/mL) |
|---|---|---|---|
| Nitazoxanide + Stimulus | 1 | 2.3 ± 0.4 | 70 ± 4 |
|  | 0.5 | 2.5 ± 0.5 | 79 ± 4 |
|  | 0.1 | 3 ± 0.2 | 83 ± 1 |
| Tizoxanide + Stimulus | 1 | 2.3 ± 0.5 | 78 ± 6 |
|  | 0.5 | 3.2 ± 0.1 | 80 ± 2 |
|  | 0.1 | 2.9 ± 0.2 | 87 ± 2 |

It can be seen from above table that HaCaT cells produced moderate levels of IL-6, very low levels of TNF-α and no IL-1β in response to IFN-γ. Reduction in IL-6 release was observed in HaCaT cells treated with 0.25 μM of Niclosamide.

Example 7: Topical and Transdermal Formulations of Antiparasitic Drugs

TABLE X

Compositions of topical and transdermal formulations

| Ingredient/Excipient | NIC-1 | NIC-2 | NIT-1 | NIT-2 |
|---|---|---|---|---|
| Niclosamide | 3% | 3% | — | — |
| Nitazoxanide | — | — | 5% | 5% |
| Petrolatum | 96% | 81% | 94% | 79% |
| Lanolin | 1% |  | 1% |  |
| Methyltriglycol |  | 5% |  | 4.5% |
| Liquid paraffin |  | 10% |  | 10.5% |
| Sorbitan sesquioleate |  | 1% |  | 1% |

The compositions NIC-1 and NIT-1 are topical dermal whereas NIC-2 and NIT-2 are transdermal compositions.

Example 8: In-Vivo Evaluation of Drugs by Imiquimod Induced Psoriasis Model in Balb/c Mice In-vivo experiment to check anti-psoriatic potential of Niclosamide and Nitazoxanide was performed in *Mus Musculus* species. BALB/c mice (Sex: Female, Age: 7-8 Weeks) were used for induction of psoriasis using IMQ. Topical application of imiquimod (IMQ) in mice can induce and exacerbate psoriasis closely resembling human psoriasis. Concurrent treatment with various concentrations of Niclosamide and Nitazoxanide were investigated to quantify the reduction in parameters of psoriasis in the IMQ induced mice. Nine groups (8 animals per group) were used including normal control, disease control; three concentrations of Niclosamide, viz 1%, 2% and 3%; three concentrations of Nitazoxanide, viz. 3%, 4% and 5% and positive control of Tenovate (Clobetasol) 0.05% cream. In all 63 mg cream containing 5% of IMQ was applied to dorsal area (shaved back) and right ear for 8 days. Topical formulations from Example 7 were used during this experiment. Three hours after IMQ application, different doses of Niclosamide (1%, 2% and 3%) and Nitazoxanide (3%, 4% and 5%) were applied to dorsal area (50 mg) and ear (25 mg) in the corresponding groups. The Niclosamide, Nitazoxanide or vehicle doses were applied twice daily.

The parameters investigated were ear thickness change, % inhibition of ear inflammation, Psoriatic Area Severity Index (PASI). Histopathology was performed of right ear and dorsal skin by H & E staining. The biomarker in this study was inflammatory cytokine IL-23 analyzed by ELISA obtained from tissue lysate of ear region where IMQ and doses were applied.

The results of in-vivo studies for Niclosamide and Nitazoxanide are given in table X:

TABLE XI

Parameters evaluated in IMQ induced psoriasis assay for Niclosamide and Nitazoxanide.

| Group | % Body Weight Change | Spleen weight (mg) | % inhibition of Ear inflamn. | PASI score | IL23 Levels (pg/ml) | Histopathology Scores | | |
|---|---|---|---|---|---|---|---|---|
|  |  |  |  |  |  | Hyperkeratosis | Epidermal Thickness | Rete Peg Prolifern. |
| Normal Control | 10.8 | 141.6 ± 15.5 | 100.0 | 0.00 | 83.9 ± 6.8 | 1.00 ± 0.0 | 4.13 ± 0.1 | 0.00 |
| Disease Control | -1.9 | 222.5 ± 19.3 | 0.0 | 20.3 ± 1.6 | 249.5 ± 52.0 | 1.7 ± 0.2 | 6.7 ± 0.2 | 1.7 ± 0.2 |
| Niclosamide 1% | -6.0 | 265.2 ± 49.2 | 27.1 | 15.8 ± 3.0 | 119.9 ± 7.8* | 0.8 ± 0.2[#] | 6.8 ± 0.2 | 1.8 ± 0.2 |
| Niclosamide 2% | -7.5 | 214.4 ± 15.1 | 30.4 | 17.2 ± 1.7 | 96.6 ± 10.9* | 1.4 ± 0.2 | 5.6 ± 0.8 | 1.4 ± 0.2 |
| Niclosamide 3% | -6.0 | 229.7 ± 18.7 | 42.7 | 10.7 ± 4.1* | 83.6 ± 9.8* | 1.0 ± 0.0[$] | 5.2 ± 0.2 | 0.5 ± 0.2[#] |
| Nitazoxanide 3% | -4.75 | 203.6 ± 22.6 | -5.9 | 14.2 ± 5.1[#] | 147.79[#] | 1.0 ± 0.0[$] | 5.6 ± 0.4 | 1.2 ± 0.2 |
| Nitazoxanide 4% | -0.59 | 274.7 ± 54.3 | 26.1 | 21.5 ± 3.4 | 128.67* | 1.3 ± 0.2 | 4.7 ± 0.3[#] | 1.0 ± 0.3 |
| Nitazoxanide 5% | -3.78 | 204.1 ± 15.3 | 40.9 | 13.1 ± 1.6* | 89.45* | 1.1 ± 0.1 | 5.3 ± 0.6 | 1.1 ± 0.1 |
| Clobetasol 0.05% | -16.9 | 49.3 ± 10.3 | 86.9 | 4.83 ± 2.3 | 64.1 ± 7.4 | 1.0 ± 0.0* | 4.3 ± 0.3[#] | 0.3 ± 0.3[#] |

*$p < 0.001$,
[#]$p < 0.01$,
[$]$p < 0.05$;
one Way ANOVA followed by Dunett's test, compared to Disease control The above results from Table XI show that both Niclosamide and Nitazoxanide have good ability to inhibit proliferation of skin thickening and reduce inflammatory processes in disease, thus demonstrating anti-psoriatic potential of the drugs. The tested drugs showed dose dependent reduction in ear inflammation at Day 7. Niclosamide and Nitazoxanide inhibited 42.7% and 40.9% of the ear inflammation respectively at highest tested concentrations. Psoriatic area severity index (PASI) scores in the treatment groups show significant reduction in severity of disease. Niclosamide showed up to 50%/a reduction in the PASI score at 3% concentration indicating anti-psoriatic potential. A significant increase was observed in IL-23 levels (p<0.001) on Imiquimod application in ear tissue homogenates. The animals treated with the Niclosamide and Nitazoxanide at different doses showed significant (p<0.01, p<0.001 respectively) reduction of IL-23 level. Niclosamide treatment showed dose dependent response where in the highest concentration reduced the IL23 levels to normal control suggesting ability of the compound to reduce inflammation. On the other hand, Clobetasol reduces IL-23 levels below that of normal control indicating that this may hamper safety of the drug. The inhibition of IL-23 by compounds of Formula-I leads to anti-inflammatory action seen in this disease model. The concentration dependent reduction of cytokine IL-23 by both Niclosamide and Nitazoxanide indicate their potential in treatment of diseases associated with upregulation of IL-17/IL-23 axis including skin diseases like psoriasis, rosacea and eczema.

The results from Table XI demonstrated that no significant body weight change was observed in the Niclosamide and Nitazoxanide groups; whereas Clobetasol showed significant body weight change from Day 7 to Day 9 (p<0.01, p<0.001). The significant reduction in body weight of Clobetasol group is an indicator of drug toxicity. On Day 9, all the experimental animals were euthanized, spleen was collected and weighed. Among the multiple treatment groups; marginal reduction in spleen weight was observed in treatment with Niclosamide 2%, Nitazoxanide 3% and 5%, however it was not statistically significant when compared with disease control. The reduction in spleen weight was observed to be significant in Clobetasol group indicating deleterious effects on spleen cells.

The histopathology studies of the ear lobes were performed and critical parameters like Hyperkeratosis, Epidermal Thickness and Rete peg proliferation were recorded. The evaluation shows dose dependent reduction in Epidermal thickness and Rete peg Proliferation. A significant reduction in Hyperkeratosis was shown by both Niclosamide and Nitazoxanide. Thus, compounds of Formula-I such as Niclosamide and Nitazoxanide exhibit anti-psoriatic potential with good safety profile.

It will be appreciated that, although specific embodiments of the invention have been described herein for purposes of illustration, various modifications may be made without departing from the spirit and scope of the invention. All such modifications and variations are intended to be included herein within the scope of this disclosure.

The invention claimed is:

1. A method of treating phosphodiesterase related disorders in a mammal, comprising administering to a mammal in need of such treatment a therapeutically effective amount of a composition comprising an anti-parasitic compound having phosphodiesterase inhibitory activity;
   wherein the anti-parasitic compound having phosphodiester inhibitory activity is administered to a mammal by an oral route in a dosage of about 1 mg to 3000 mg daily in the form of oral solution, suspension, syrup, dental paste or a capsule; or
   is administered to a mammal by an ophthalmic route in a concentration of about 0.001% to 10.0% w/v in the form of eye drops or eye gel; or
   is administered to a mammal by a topical route in a concentration of about 0.001% to 20.0% w/w in the form of a cream, gel, patch, ointment, topical swab, emulsion, solution, paste, shampoo, or spray with or without applicator; or
   is administered to a mammal by an intravenous, intradermal, intralesional or subcutaneous route in a concentration of about 0.001% to 5.0% w/v in the form of an injection or infusion; or
   is administered to a mammal as an inhaler, nebulizer, or vaporizer in a concentration of about 0.001% to 5.0% w/w.

2. The method of claim 1, wherein the anti-parasitic compound has the structure of Formula I

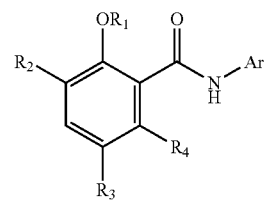

wherein $R_1$ is —H; $R_2$ is selected from —H, —Cl, —Br; $R_3$ is selected from —H, —Cl, —Br; $R_4$ is selected from —H, —Cl; Ar is

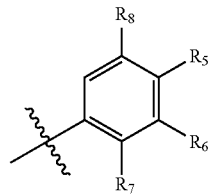

wherein $R_5$ is selected from —H, —NO$_2$, —Br; $R_6$ is selected from —H, —Cl; $R_7$ is selected from —H, —OH, —Cl; $R_8$ is selected from —H, —Cl; and enantiomers, diastereomers, prodrugs or metabolites thereof, or pharmaceutically acceptable salts, solvates and polymorphs thereof in a pharmaceutically acceptable carrier, vehicle, or diluents.

3. The method of claim 2, wherein the compound of formula I is selected from the group consisting of Niclosamide, Oxyclozanide, Dibromsalan, Metabromsalan, and Tribromsalan, and pharmaceutically acceptable salts, solvates and polymorphs thereof.

4. The method of claim 1, wherein the phosphodiesterase related disorder is selected from the group consisting of Asthma, Bronchitis, Chronic obstructive pulmonary disease (COPD), Pulmonary arterial hypertension, Allergic rhinitis, Allergic conjunctivitis, Dry eye disorder, Coronary heart disease, Intermittent claudication, Dementia, Depression, Schizophrenia, Erectile dysfunction, Duchenne muscular dystrophy, Male and female fertility disorders, Psoriasis, Eczema, Rosacea, fibrotic skin disease, Alopecia areata, Lichen Planus, Pemphigus foliaceus, Pemphigus vulgaris, Chronic periodontitis, Dermatitis Herpetiformis, Vitiligo and Bullous Pemphigoid.

5. The method of claim 1, wherein the mammal is a primate, canine, feline, bovine, ovine, porcine, camelid, caprine, rodent or equine.

6. The method of claim 4, wherein the phosphodiesterase-related disorder is selected from Psoriasis, Rosacea and Eczema.

7. The method of claim 4, wherein the phosphodiesterase related disorder is selected from Alopecia areata, Lichen Planus, Pemphigus foliaceus, Pemphigus vulgaris, chronic periodontitis, Dermatitis Herpetiformis, Vitiligo, Bullous Pemphigoid, and the fibrotic skin disease is selected from the group consisting of Keloids, Hypertrophic scarring, Collagenoma, and Scleroderma.

8. A method of treating phosphodiesterase related disorders in a mammal comprising topical application of a composition comprising niclosamide 3%, petrolatum 96% and lanolin 1% to a mammal in need of such treatment.

* * * * *